United States Patent [19]

Rosenberger

[11] 4,025,564

[45] May 24, 1977

[54] TRIDEHYDRO-CANTHAXANTHIN

[75] Inventor: Michael Rosenberger, Caldwell, N.J.

[73] Assignee: Hoffmann-La Roche Inc., Nutley, N.J.

[22] Filed: Sept. 15, 1976

[21] Appl. No.: 723,416

Related U.S. Application Data

[62] Division of Ser. No. 585,224, June 9, 1975, Pat. No. 4,000,198.

[52] U.S. Cl. .................. 260/586 R; 260/606.5 F
[51] Int. Cl.$^2$ .................. C07C 49/48; C07C 49/54
[58] Field of Search ............................ 260/586 R

[56] References Cited

UNITED STATES PATENTS

| 3,478,104 | 11/1969 | Surmatis | 260/586 R |
| 3,732,214 | 5/1973 | Surmatis et al. | 260/586 R |
| 3,941,841 | 3/1976 | Surmatis et al. | 260/586 R |

*Primary Examiner*—Norman Morgenstern
*Attorney, Agent, or Firm*—Samuel L. Welt; Bernard S. Leon; William H. Epstein

[57] ABSTRACT

A total synthesis of canthaxanthin or dinor-canthaxanthin, known food coloring agents, from pentols.

1 Claim, No Drawings

TRIDEHYDRO-CANTHAXANTHIN

This is a division of application Ser. No. 585,224 filed June 9, 1975, now U.S. Pat. No. 4,000,198.

SUMMARY OF THE INVENTION

In accordance with this invention, a method is provided for synthesizing a compound of the formula:

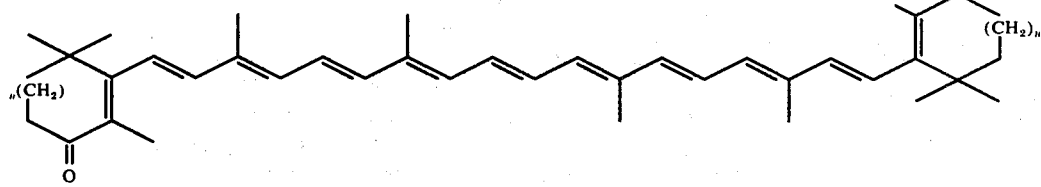

wherein $n$ is an integer of from 0 to 1,

The compound of formula I where $n$ is 1 is canthaxanthin which has the following formula:

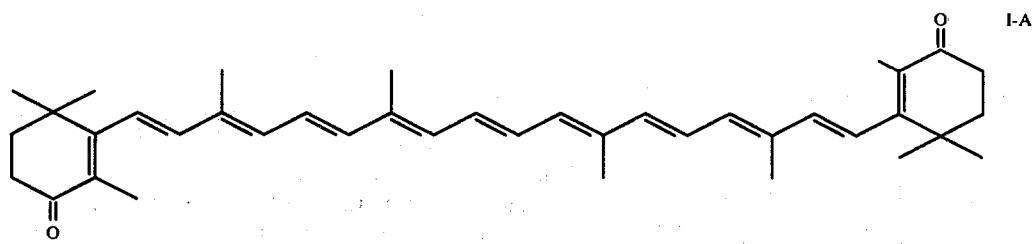

which, in accordance with this invention, can be prepared from either 3-pentol which has the formula:

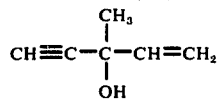
II-A or a 1-pentol which has the formula:

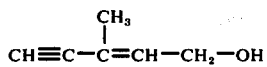
II-B via condensation with a compound of the formula:

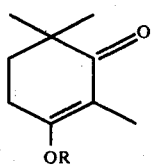
III-A wherein R is an alkyl group containing 3 to 8 carbon atoms;

or condensation with a compound of the formula:

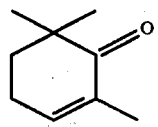
IV

The compound of formula I where $n$ is 0 is dinor-canthaxanthin and has the formula:

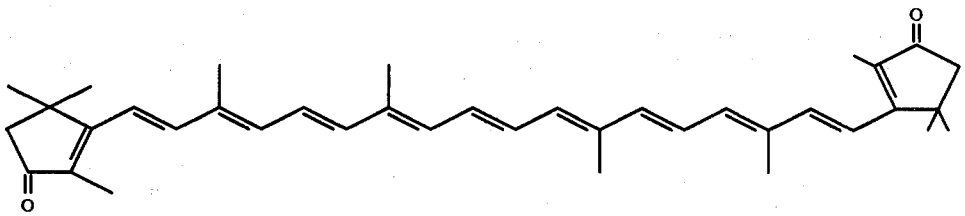

This compound can also be prepared from the compound of formula II-B by condensation with a compound of the formula:

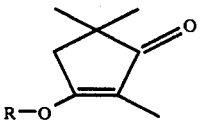
III-B wherein R is as above.

DETAILED DESCRIPTION

The term "halogen" as used throughout this specification includes all four halogens, i.e., chlorine, fluorine, bromine and iodine. The term "lower alkyl" as used herein designates a saturated aliphatic straight or branched chain hydrocarbon containing from 1 to 7 carbon atoms such as ethyl, methyl, isopropyl, etc. The term "lower alkoxy" as used throughout the specification denotes lower alkoxy groups containing from 1 to 7 carbon atoms such as methoxy, ethoxy, propoxy, isopropoxy, etc.

As used herein, the term "aryl" designates mononuclear aromatic hydrocarbon groups such as phenyl, tolyl, which can be unsubstituted or substituted in one or more positions with a halogen, nitro, lower alkyl or lower alkoxy substituent and polynuclear aryl groups such as naphthyl, anthryl, phenanthryl, which can be unsubstituted or substituted with one or more of the aforementioned groups. The preferred aryl groups are the substituted and unsubstituted mononuclear groups particularly phenyl. The term "alkali metal" includes all alkali metals such as sodium, potassium and lithium.

Dinor-canthaxanthin may be utilized as a food coloring agent in the same manner as canthaxanthin.

In accordance with a preferred embodiment of this invention, the compound of formula I is produced from a compound of formula II-B by first protecting the free hydroxy group with a hydrolyzable ether moiety to form a compound of the formula:

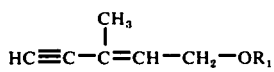   VI wherein $R_1$ is hydrogen or taken together with its attached oxygen moiety forms an ether protecting group removable by hydrolysis.

In accordance with this preferred embodiment of this invention. $OR_1$ may form an ether which upon hydrolysis yields the hydroxy group. Among the ether protecting groups are included the tetrahydropyranyl, lower alkyl or 4-methyl-5,6-dihydro-2H-pyranyl ether. Other ether groups include arylmethyl ethers such as benzyl, benzylhydryl, or trityl ethers as well as alpha-lower alkoxy-lower alkyl ethers such as methoxymethyl ethers, or methoxy ethyl ether. Among the preferred ether groups are t-butyl, benzyl and the alpha-lower alkoxylower alkyl ether groups. However, this reaction can take place where the hydroxy in the compound of formula H-B is free.

The compound of formula VI is converted to the compound of formula I via the following intermediates:

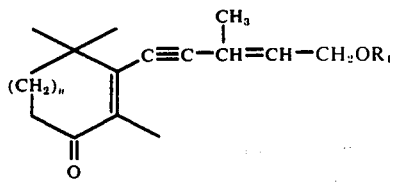   VIII

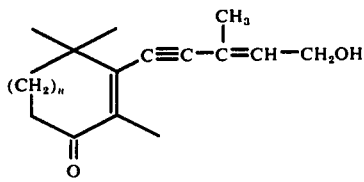   IX

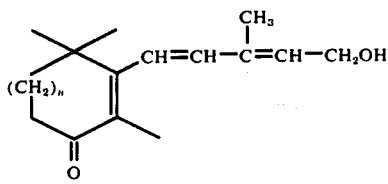   X

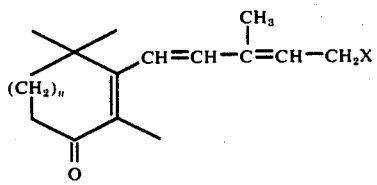   XI

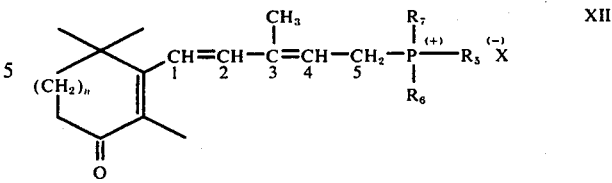   XII wherein
X is halogen,
$R_1$ is as above;
$R_5$, $R_6$ and $R_7$ are aryl or lower alkyl.

The compound of formula II-B is converted to the compound of formula VI utilizing any conventional method of etherifying a hydroxy group. Where the preferred ether group is an alpha-lower alkoxylower alkyl group, the compound of formula II-B is reacted with a vinyl ether of the formula:

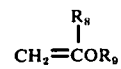

wherein $R_8$ and $R_9$ are lower alkyl.

This reaction is carried out in the presence of an acid catalyst. Any conventional acid catalyst can be utilized. Among the preferred acid catalysts are the strong organic acids such as p-toluene sulfonic acid or inorganic mineral acids such as sulfuric acid, hydrochloric acid, etc. In carrying out this reaction, temperature and pressure are not critical and this reaction can be carried out at room temperature and atmospheric pressure. If desired, higher and lower temperatures can be utilized.

The compound of formula VI is converted to the compound of formula VIII by reacting the compound of formula VI with a compound of the formula:

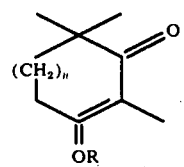   III

In this reaction, the compound of formula VI is in the following form:

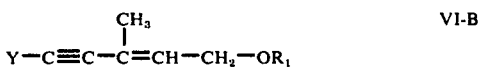   VI-B wherein
Y is MgX or an alkali metal; and
$R_1$ is as above.

The compound of formula VI-B is formed from the compound of formula VI utilizing any conventional method of forming either a Grignard salt or an alkali metal acetylide. For example, the alkali metal acetylide salt of formula VI can be formed by reacting the compund of formula VI with an alkali metal lower alkyl such as n-butyllithium in an ether solvent at temperatures of −80° to −20 C.

The reaction of the compound of formula VI-B with the compound of formula III to produce a compound of the formula VIII is carried out utilizing conventional Grignard conditions. Any of the conditions conventional in Grignard reactions can be utilized in carrying out this reaction. Among the preferred condition for carrying out this reaction is utilizing an inert organic solvent medium. Any conventional inert organic solvent medium can be utilized. Among the preferred solvents are the ether solvents such as diethyl ether, tetrahydrofuran, etc. Other solvents which can be utilized are the hydrocarbon solvents such as benzene, toluene, etc. In general, this reaction can be carried out at room temperature and atmospheric pressure. On the other hand, elevated or reduced temperatures can be utilized. Generally, it is preferred to carry out this reaction at a temperature of from −50° to +50° C.

Where $R_1$ is an ether protecting group, the compound of formula VIII can be converted to the compound of formula IX by conventional ether hydrolysis. Any method conventionally utilized to cleave ether groups can be utilized to carry out this conversion. Among the preferred methods is to treat the compound of formula VIII with an aqueous inorganic acid such as dilute hydrochloric acid, dilute sulfuric acid, etc. Generally, this reaction is carried out in an aqueous medium. In carrying out this reaction, temperature and pressure are not critical and this reaction can be carried out at room temperature and atmospheric pressure.

The compound of formula IX is converted to the compound of formula X by partially hydrogenating the compound of formula IX. Any conventional method of partial hydrogenation can be utilized in carrying out this reaction. Generally, this reaction is carried out by hydrogenating in the presence of a selective hydrogenation catalyst, e.g., a palladium lead catalyst in the presence of quinoline, of the type disclosed in Helvetica Chemica Acta; 35 446 (1952). The selective hydrogenation of the triple bond of the compound of formula IX when converted to the compound of formula XII produces a double bond at the 1,2 position of the compound of formula XII having a trans configuration.

The compound of formula X is converted to the compound of formula XI by treating the compound of formula X with a halogenating agent. Any of the conditions conventional in halogenating an alcohol can be utilized to carry out this reaction. Among the conventional halogenating agents which can be utilized are included phosphorous tribromide, triphenyl phosphine dibromide and thionyl chloride. Any of the conditions conventional in utilizing these halogenating agents can be used to convert the compound of formula X to the compound of formula XI.

The compound of formula XI is converted to the compound of formula XII by treating the compound of formula XI with a phosphine or treating the compound of formula X with an acid addition salt of a phosphine. Any method conventional in forming phosphonium salts can be utilized in this conversion.

The compound of formula I is formed from the compound of formula XII by reacting the compound of formula XII with a compound of the formula:

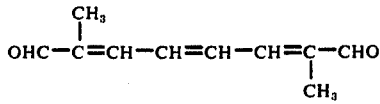

via a Wittig reaction.

This reaction is carried out utilizing conditions that are conventional in Wittig type reactions. In this reaction, two moles of the compound of formula XII are reacted per mole of the compound of formula XIII.

Where the 1-pentol of formula H-B has a trans configuration about the double bond contained therein, this trans configuration is carried out through this synthesis to its conversion to the compound of formula I. Hence, compounds of formula VIII and formula IX produced thereby have a trans configuration about the double bond. The compound of formula IX having the trans configuration is converted to the compound of formula I with this same trans configuration intact. On the other hand, where the compound of formula II-B has a cis configuration, this cis configuration is maintained about this double bond throughout the conversion of the compound of the formula II-B to the compound of formula I. The compound of formula I which contains cis double bonds can be directly isomerised to the compound of formula I having an all trans configuration by conventional methods such as heating in water or in an organic solvent medium.

The compound of formula III-A can be prepared via the reaction of a compound of formula:

wherein $R_{10}$ is lower alkyl;
with a compound of the formula:

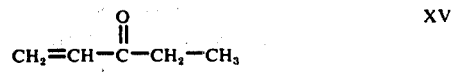

to produce a compound of the formula:

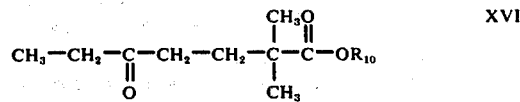

wherein $R_{10}$ is as above.

The compound of formula XIV is reacted with the compound of formula XV to produce a compound of the formula XVI by Michael addition. Generally, this reaction is carried out in the presence of an alkali metal amide such as the alkali metal lower alkyl amide. Among the preferred amides are sodium-diethylamide, lithiumdiisopropylamide, etc. Generally, this reaction is carried out in an inert solvent. Any conventional inert solvent can be utilized. Among the preferred solvents are the ether solvents such as dioxane, tetrahydrofuran, etc. In general, the alkali metal alkyl amides can be generated in the reaction medium by adding an alkali metal alkyl or phenyl and an alkyl amine.

Any conventional alkyl amine such as the lower alkyl amines and any conventional alkali metal lower alkyl can be utilized in this reaction. Among the preferred alkyl amines are included ethyl amine, n-butyl amine and diisopropyl amine. Among the preferred alkali metal lower alkyls or phenyls are included n-butyl lithium, n-phenyl sodium. This reaction can be carried out at temperatures of from −120° to −60° C.

The compound of formula XVI is converted to the compound of formula III-A via the following intermediate:

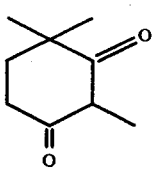

XVII

The compound of formula XVI is converted to the compound of formula XVII by treating the compound of the formula XVI with an alkali metal hydride such as sodium hydride. Generally, this reaction is carried out in an inert organic solvent. Any conventional inert organic solvent can be utilized. Among the preferred inert organic solvents are the ether solvents such as diethyl ether, tetrahydrofuran, etc. Generally, this reaction is carried out by refluxing the compound of formula XVI in the presence of the alkali metal hydride in the ether solvent. Depending upon the ether solvent, the refluxing can be carried out at a temperature of from 35° to 80° C.

The compound of formula XVII is converted to the compound of formula III-A by etherifying the compound of formula III-A. Any conventional method of etherifying can be utilized to carry out this reaction. Generally the etherification is carried out by treating the compound of formula XVII with a lower alkanol containing from about 3 to 7 carbon atoms. Generally, it is preferred to utilize lower alkanols containing 3 to 7 carbon atoms since they preferentially etherify one of the two oxo groups to produce a compound of formula III-A. Generally, this reaction is carried out by condensing the alcohol with the compound of formula XVII in the presence of an acid catalyst. Any conventional acid catalyst can be utilized. Among the preferred acid catalysts are p-toluene sulfonic acid and acid forms of ion exchange resins. This reaction can be carried out by removing the water formed from the reaction. Any conventional method for removing the water formed during this reaction can be utilized. Among the preferred methods for removing water is by azeotropic distillation utilizing solvents which form an azeotrope such as benzene, toluene, xylene as well as other aromatic hydrocarbon solvents. Any conventional method of azeotropic distillation can be utilized to carry out this procedure. Where water is formed by azeotropic distillation, the reaction is generally carried out in any conventional solvent capable of forming an azeotrope with water. Furthermore, in this case, the reaction is carried out at the reflux temperature of the azeotropic mixture.

The compound of formula III-B is prepared from a compound of the formula:

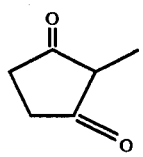

XVIII via an intermediate of the formula:

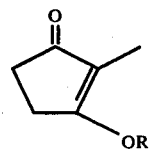

XIX wherein R is as above.

The compound of formula XVIII is converted to the compound of formula XIX in the same manner as described in connection with the conversion of a compound of the formula XVII to a compound of formula III-A.

The compound of formula XIX is converted to a compound of formula III-B by treating the compound of formula XIX with an alkali metal alkyl amide and a methyl halide. In carrying the process of this invention, the alkali metal lower alkyl amides are generally preferred. Among these alkali metal lower alkyl amides, diisopropyl lithium amide is particularly preferred. In carrying out this reaction, two moles of the methyl halide are reacted with one mole of the compound of formula XIX. Generally, this reaction is carried out in an organic solvent. Any conventional inert organic solvent can be utilized. Among the preferred solvents are included ether solvents such as diethyl ether, tetrahydrofuran, etc. This reaction is carried out at temperatures of from about −80° to about 30° C., with temperatures of from about −70° to about 40° C. being preferred.

In accordance with another embodiment of this invention, the compound of formula I-A can be prepared from a compound of formula II-A via the following intermediates;

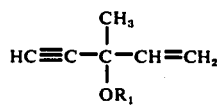

XXI

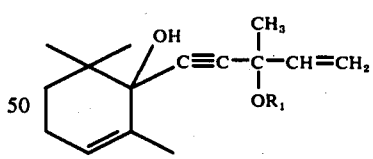

XXII

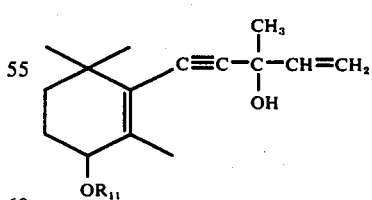

XXIII

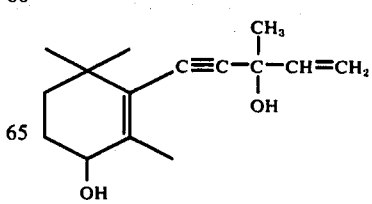

XXIV

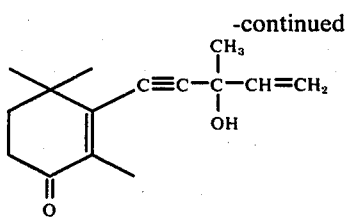 XXV

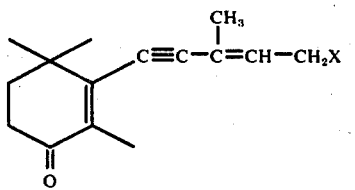 XXVI

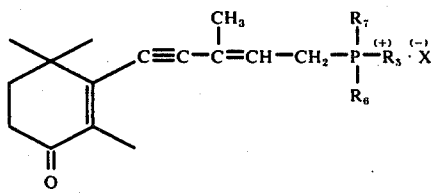 XXVII

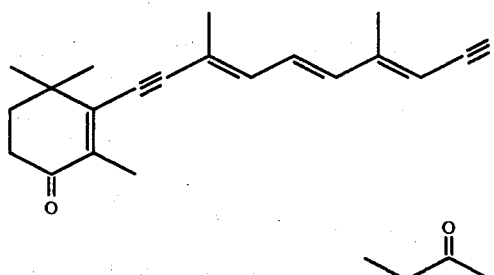 XXVIII wherein X, $R_1$, $R_5$, $R_6$ and $R_7$ are as above and $R_{11}$ is lower alkanoyl.

The compound of formula II-A is converted to the compound of the formula XXI by etherification in the manner described in connection with the conversion of the compound of the formula II-B to the compound of the formula VI. In carrying out this reaction, any conventional method of etherifying a hydroxy group can be utilized. The preferred ether group formed by $R_1$ is an alpha-lower alkoxy lower alkyl ether and it is formed in the same manner described in connection with the formation of a compound of the formula VI.

The compound of the formula XXI is reacted with 2,6,6-trimethylcyclohexen-2-en:1-one utilizing a magnesium halide or alkali metal salt of the compound of the formula XXI. This reaction is carried out utilizing conventional Grignard conditions.

The compound of formula XXII is converted to the compound of the formula XXIII by treating with a lower alkanoic acid, preferably acetic acid. In carrying out this reaction, the lower alkanoic acid is utilized as the solvent medium. In carrying out this reaction, temperature and pressure are not critical and this reaction can be carried out under room temperature and atmospheric pressure. If desired, higher or lower temperatures can be utilized. In general, the reaction is carried out at from about 10° to 70° C.

The compound of formula XXIII is converted to the compound of the formula XXIV utilizing basic hydrolysis. Any conventional method of basic hydrolysis can be utilized to carry out this conversion. Generally it is preferred to treat the compound of formula XXIV in an aqueous medium with an alkali metal hydroxide such as potassium or sodium hydroxide. In carrying out this hydrolysis reaction, temperature and pressure are not critical and this reaction can be carried out at room temperature and atmospheric pressure. On the other hand, elevated or reduced temperatures can be utilized.

The compound of the formula XXIV is converted to the compound of formula XXV by oxidation with chromium trioxide or manganese dioxide. Any of the conditions conventional in oxidizing with these oxidizing agents can be utilized to carry out this conversion.

On the other hand, the compound of formula XXV can be formed from the compound of formula XXI by first converting the compound of formula XXI to a compound of the formula:

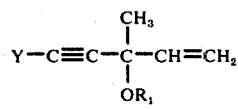 XXI-A wherein Y and $R_1$ are as above;

and reacting the compound of formula XXI-A with a compound of the formula III-A to form an intermediate of the formula:

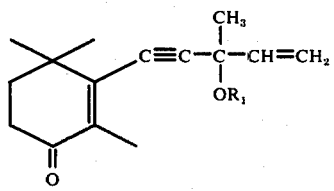 XXIX wherein $R_1$ is as above.

The compound of formula XXI is converted to the compound of formula XXI-A in the same manner as described in connection with the conversion of a compound of the formula VI to a compound of the formula VI-B. The reaction of the compound of the formula XXI-A with a compound of the formula III-A is carried out in the same manner as described hereinbefore in connection with the reaction of a compound of the formula III with a compound of the formula VI-B to form a compound of the formula VIII. The reaction of the compound of the formula XXI-A with a compound of the formula III-A forms the compound of the formula XXIX. Where $R_1$ forms an ether protecting group, the compound of the formula XXIX is converted by acid hydrolysis to form the compound of the formula XXV. This acid hydrolysis can be carried out by treating the compound of the formula XXIX with an organic or mineral acid. This hydrolysis is carried out in the same manner as described in connection with the conversion of the compound of the formula VIII to a compound of the formula IX.

The compound of the formula XXV is converted to a compound of the formula XXVI by treating the compound of the formula XV with a halogenating agent in the same manner as described hereinbefore in connection with the conversion of a compound of the formula X to a compound of the formula XI. The compound of the formula XXVI is converted to the compound of the formula XXVII by forming the phosphine salt in the same manner as described in connection with the conversion of a compound of the formula XI with a compound of the formula XII. The compound of the formula XXVII can be reacted via a Wittig reaction with a compound of the formula:

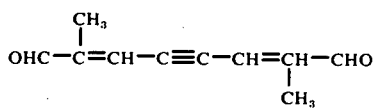     XXXV to produce a compound of the formula XXVIII. This reaction is carried out in the same manner as described in connection with the conversion of a compound of the formula XII to a compound of the formula I. The compound of formula XXVIII is converted by selective hydrogenation to the compound of formula I-A. This reaction is carried out in the same manner as described in connection with the conversion of the compound of the formula IX to a compound of the formula X.

The following Examples are illustrative but not limitative of the present invention. All temperatures are in degrees Centigrade (°C.) and the ether utilized is diethyl ether.

The term "concentrated aqueous hydrochloric acid" designates 10 or more molar hydrochloric acid. The term "Lindlar catalyst" designated a catalyst prepared from palladium chloride, calcium carbonate and lead acetate as described in Organic Synthesis Collective Volume 5, page 880–893 (1973).

EXAMPLE 1

1-Ethoxy-1-(3-methyl-4-trans-penten-1-yn-1-oxy)ethane

Ethyl vinyl ether (35 ml) was cooled to 5° and treated with p-toluenesulfonic acid (PTSA; monohydrate; 100 mg) followed by the slow addition of freshly distilled 3-methyl-2-trans-penten-4-yn-1-ol (>95% trans; 20g). After the exothermic reaction had subsided the mixture was left at room temperature for 10 min., quenched with triethylamine (.5 ml) and distilled to yield 1-ethoxy-1-(3-methyl-4-trans-penten-1-yn-1-oxy)ethane (32.1g) bp 44°–45° C.

EXAMPLE 2

By reacting ethyl vinyl ether with 3-methyl-4-penten-1-yn-3-ol in the manner of Example 1, the compound 1-ethoxy-1-[3-methyl-4-penten-1-yn-3-oxy]ethane was produced.

EXAMPLE 3

1-Ethoxy-[1-(2,6,6-trimethyl-1-hydroxy-2-cyclohexen-1-yl)-3-methyl-4-penten-1-yn-3-oxy]ethane The compound 1-ethoxy-1-[3-methyl-4-penten-1-yn-3-oxy]ethane (3.4g) was dissolved in diethyl ether (30 ml), cooled to −60°, treated with a solution of n-butyllithium (10.6 ml; 1.9M in hexane), warmed to 0°, and stirred for 5 min. This clear solution of the lithium salt was then cooled to −20° and exposed to 2,6,6-trimethylcyclohex-2-en-1-one (2.28) dissolved in diethyl ether (5 ml).

After complete addition, the reaction mixture was stirred at room temperature for 1 hr, quenched with acetic acid (10 ml; at 20° C) and stirred a further 16 hr at room temperature (10 min is sufficient). Dilution with brine and more ether yielded 1-ethoxy[1-(2,6,6-trimethyl-1-hydroxy-2-cyclohexen-1-yl)-3-methyl-4-penten-1-yn-3-oxy]ethane (5.5g) on removal of the solvents "in vacuo".

EXAMPLE 4

1-(2,6,6-Trimethyl-3-acetoxycyclohexen-1-yl)3-methyl-4-penten-1-yn-3-ol

The compound 1-ethoxy-[1-(2,6,6-trimethyl-1-hydroxy-2-cyclohexen-1-yl)-3-methyl-4-penten-1-yn-3-oxy]ethane (9.5g) in acetic acid (40 ml) was heated at 55° for 1½ hr and then taken to dryness "in vacuo" (45° at .5 mmHg), dissolved in hexane, and chromatographed on silica gel (400 g). Elution with hexane-ether mixtures (4:1 parts by volume and 3:1 parts by volume 500 ml cuts, 2 liters) yielded 1-(2,6,6-trimethyl-3-acetoxycyclohexen-1-yl)-3-methyl-4-penten-1-yn-3-ol (4.3g) bp (4.3g) bp 165° (0.09 mmHg).

EXAMPLE 5

1-(2,6,6-Trimethyl-3-oxocyclohexen-1-yl)-3-hydroxy-3-methyl-4-penten-1-yne

The compound 1-(2,6,6-trimethyl-3-acetoxycyclohexen-1-yl)-3-methyl-4-penten-1-yn-3-ol (4.1g) dissolved in methanol (15 ml) was treated with a solution of potassium hydroxide (1.5 g) in water (5 ml) and left at room temperature for 3 hr.

Water was added and the organic materials were extracted into ether. Removal of the solvents "in vacuo" yielded the diol i.e., 1-(2,6,6-trimethyl-3-hydroxycyclohexen-1-yl)-3-hydroxy-3-methyl-4-penten-1-yne (3.45 g).

The diol (3.4 g) was dissolved in dichloromethane (20 ml) and added to a mixture of chromium trioxide (3 g), pyridine (6g) in dichloromethane (100 ml) at 10° C. The mixture was stirred at room temperature for 2 hr and then worked by the addition of ether filtration of solids and evaporation of solvent to yield 1-(2,6,6-trimethyl-3-oxocyclohexen-1-yl)-3-hydroxy-3-methyl-4-penten-1-yne contaminated by starting material. Chromatography on silica gel (150 g) yielded the pure 1-(2,6,6-trimethyl-3-acetoxycyclohexen-1-yl)3-methyl-4-penten-1-yn-3-ol (2.7 g) on elution with 30% by volume and 40% by volume ether-hexane mixtures; bp 160°–165° (0.01 mmHg).

EXAMPLE 6

2,2-Dimethyl-5-oxaheptenoic acid methyl ester

A solution of n-butyllithium in hexane (224 ml; 2.2M) was added to tetrahydrofuran (THF, 300 ml) at −60° followed by diisopropylamine (52 g) and this mixture was then warmed to room temperature stirred for 5 min and then cooled to −72° C. Methylisobutyrate (50 g) was then slowly added and the mixture was stirred for 1½ hr at −70° C. Freshly distilled ethyl vinyl ketone (42 g) in THF (60 ml) was added to the above mixture over 10 min and the mixture was then stirred for a further ½ hr at −60° C and subsequently at room temperature for 2 hr.

After this time the reaction was quenched with aqueous acetic acid and brine (Ph~9) and extracted with ether. The ether layer was washed with a saturated brine solution, dried over anhydrous magnesium sulfate and then concentrated "in vacuo". Distillation of the residue (~90g) through a 6 inch vacuum jacketed vigreaux column yielded the pure ketoester 2,2- dimethyl-5-oxaheptenoic acid methyl ester (81 g) bp 65°–66°.

EXAMPLE 7

2,6,6-Trimethylcyclohexen-1,3-dione

Sodium hydride (15.4 g); 57% by weight dispersion in oil) was washed with hexane treated with ether (350 ml) and 2,2-dimethyl-5-oxaheptanoic acid methyl ester; (62 g) and heated at reflux (mechanical stirrer essential) for 3 hr (methanol; ½ ml added to initiate the reaction). The whole reaction mixture set to a solid paste and was cooled in ice and treated with water. The ether layer was washed twice with more water and the combined aqueous extracts were reextracted with ether. Removal of the ether "in vacuo" yielded the neutral material (2.5 g) which was discarded. The aqueous extract was acidified with ice cold sulfuric acid (6M to pH~1) and the organic materials were isolated with ether. Removal of the solvents "in vacuo" gave the diketone 2,6,6-trimethylcyclohexen-1,3-dione,~50g) as a solid. This material was digested with cold (−10° to −0°) isopropyl ether (100 ml) and filtered to furnish 2,6,6-trimethylcyclohexen-1,3-dione (43.6g) mp 115°–116° C.

EXAMPLE 8

2,6,6-Trimethyl-3-isobutoxycyclohex-2-en-1-one

The compound 2,6,6-trimethylcyclohexen-1,3-dione (43.6 g) was added to a mixture of benzene (250 ml), isobutanol (50 ml) and PTSA (500 mg) and heated under reflux for 3 hr in conjunction with a Dean and Stark water separator. The reaction was then cooled to room temperature, washed with aqueous sodium carbonate solution and brine and taken to dryness "in vacuo". Distillation of residue through a 6 inch vacuum jacketed vigreaux column yielded pure 2,6,6-trimethyl-3-isobutoxycyclohex-2-en-1-one(54.6 g) bp 104°–107°.

EXAMPLE 9

5(2,6,6-Trimethyl-3-oxocyclohexen-1-yl)-3-methyl-2-trans-penten-4-yn-1-ol

The acetal compound, 1-ethoxy-1-(3-methyl-4-trans-penten-1-yn-1-oxy)ethane (18.6 g) was dissolved in ether (100 ml), cooled to −60° and treated with an n-butyllithium solution (52.5 ml, 2.2 M in hexane) and then stirred at room temperature for 15 min. This clear, pale yellow colored solution was then cooled to −10°, exposed to the enol ether 2,6,6-trimethyl-3-isobutoxycyclohex-2-en-1-one (21 g) dissolved in ether (50 ml), warmed to room temperature and stirred 1 hr more. Dilution with brine and extraction into ether yielded 5(2,6,6-trimethyl-3-oxocyclohexen-1-yl)-3-methyl-2-trans-penten-4-yn-1-ol (37 g) which was then dissolved in acetone (140 ml), added to dilute aqueous sulfuric acid (5% by weight 75 ml) and left at room temperature for 16 hr (6–8 hr is sufficient). Most of the acetone was then removed "in vacuo" and the residue was quenched with brine and extracted into ether. Removal of the solvents yielded 5(2,6,6-trimethyl-3-oxocyclohexen-1-yl)-3-methyl-2-trans-penten-4-yn-1-ol as yellow crystals which on crystallization from acetone-water (1:1 parts by volume) gave 5-(2,6,6-trimethyl-3-oxocyclohexen-1-yl)-3-methyl-2-trans-penten-4-yn-1-ol (20.5 g) mp 102°–105° C.

EXAMPLE 10

Preparation of 1-(2,6,6-trimethyl-3-oxocyclohexen-1-yl)-3-hydroxy-3-methyl-4-penten-1-yne The mixed acetal 1-ethoxy-1-[3-methyl-4-penten-1-yn-3-oxy]ethane (38 g) dissolved in ether (200 ml) was converted to the lithium salt with n-butyllithium (103 ml, 2.2M hexane) as in Example 9. Addition of the ketone 2,6,6-trimethyl-3-isobutoxycyclohex-2-en-1-one (35.9 g) in ether (100 ml) and proceeding as before yielded the crude adduct which was dissolved in acetic acid (150 ml) and heated at 60° C for 1 hr. The solvents were removed "in vacuo" and the residue was distilled with a Kugel Rohr to furnish pure 1-(2,6,6-trimethyl-3-oxocyclohexen-1-yl)-3-hydroxy-3-methyl-4-penten-1-yne (33.5 g) bp 150°–165° C (0.03 mmHg).

EXAMPLE 11

5-(2,6,6-Trimethyl-3-oxocyclohexen-1-yl)-3-methyl-2-penten-4-yne-1-triphenylphosphonium bromide The alcohol, 1-(2,6,6-trimethyl-3-oxocyclohexen-1-yl)-3-hydroxy-3-methyl-4-penten-1-yne (450 mg) was dissolved in ether (15 ml), treated with pyridine (1 drop) and exposed to phosphorous tribromide (550 mg) in ether (2 ml) at 0° C and then stirred a further 15 min at room temperature. Extraction of the ether with water and aqueous sodium carbonate solution (10% by weight) yielded the bromide, 5-(2,6,6-trimethyl-3-oxocyclohexen-1-yl)-3-methyl-2-penten-4-yne-1-bromide (~500 mg) as a mixture of cis and trans isomers. This material was dissolved in ethyl acetate (0.5 ml) and added to triphenylphosphine (600 mg) dissolved in more ethyl acetate (1.5 ml) and heated to 35° C and left at room temperature for 3 hr. Ether was added and the solids were separated by decantation to yield the 5-(2,6,6-trimethyl-3-oxocyclohexen-1-yl)-3-methyl-2-penten-4-yne-1-triphenylphosphonium bromide (800 mg).

EXAMPLE 12

Preparation of 1,18-Bis-(2,6,6-trimethyl-4-oxo-1-cyclohexen-1-yl)-3,7,12,16-tetramethyl-3,5,7,11,13,15-octadecahexaene-1,9,17-triyne The salt from 5-(2,6,6-trimethyl-3-oxocyclohexen-1-yl)-3-methyl-2-penten-4-yne-1 -triphenylphosphonium bromide (612 mg) was added to 2,7-dimethylocta-2,6-dien-4-yne-1,8-diol (81 mg) dissolved in methanol (5 ml) and cooled to 0° C.

The solution of sodium methoxide (60 mg) in methanol (1 ml) was then added and after stirring 20 min the reaction products were extracted with a mixture of brine and hexane. Removal of the organic solvents "in vacuo" yielded products, i.e., 1,18-bis-(2,6,6-trimethyl-4-oxo-1-cyclohexen-1-yl)-3,7,12,16-tetramethyl-3,5,7,11,13,15-octadecahexaene-1,9,17-triyne, and 1-(2,6,6-trimethyl-4-oxo-1-cyclohexen-1-yl)-3,7,12-trimethyl-3,5,7,11-tridecatetra-1,9-diyn-1-al (320 mg) which was chromatographed on silica gel (35 g). Elution with 20% by volume ether and 80% by volume hexane mixture yielded 1-(2,6,6-trimethyl-4-oxo-1-cyclohexen-1-yl)-3,7,12-trimethyl-3,5,7,11-tridecatetra-1,9-diyn-1-al, a first product.

Further elution of the column with 30% by volume and 40% by volume ether-hexane mixtures yielded the 1,18-bis(2,6,6-trimethyl-3-oxo-1-cyclohexen-1-yl)-3,7,12,16-tetramethyl-3,5,7,11,13,15-octadecahexaene-1,9,17 triyne which after crystallization from a hexane-ether mixture had mp 95°–100° C.

EXAMPLE 13

5-(2,6,6-Trimethyl-3-oxocyclohexen-1-yl)-3-methyl-2,4-trans, trans-pentadien-1-ol The acetylenic ketone 5(2,6,6-trimethyl-3-oxocyclohexen-1-yl)-3-methyl-2-trans-penten-4-yn-1-ol (4.6 g) dissolved in toluene (80 ml) containing anhydrous potassium carbonate (1.2 g) and Lindlar catalyst (700 mg) was hydrogenated at room temperature and pressure. A rapid uptake of hydrogen was observed and no noticeable break in the curve was seen and the reaction was stopped after 3 hr when 616 ml of hydrogen had been consumed (21° C at 760 mmHg).

The solids were filtered off and the solvents removed "in vacuo" to yield a crude product which contained starting material, over-reduced products 5-(2,6,6-trimethyl-3-oxocyclohexen-1-yl)-3-methyl-2,4-trans,-trans-pentadiene-1-ol.

Chromatography on silica gel (400 g) yielded 5-(2,6,6-trimethyl-3-oxocyclohexene-1-yl)-3-methyl-2,4-trans,trans-pentadien-1-ol on elution with a 75% by volume ether-25% by volume hexane mixture (3.35 g).

EXAMPLE 14

5-(2,6,6-Trimethyl-3-oxocyclohexen-1-yl)-3-methyl-2,4-pentadien-1-triphenylphosphonium bromide The alcohol 5-(2,6,6-trimethyl-3-oxocyclohexen-1-yl)-3-methyl-2,4-trans,trans-pentadien-1-ol (3.2 g) in ether (25 ml) was cooled to −60° C, treated with PBr$_3$ (2.5 ml) dissolved in more ether (10 ml) and then warmed to room temperature over 5 min. Water was added carefully and the organic materials were isolated with ether. Removal of the solvents "in vacuo" yielded 5-(2,6,6-trimethyl-3-oxocyclohexen-1-yl)-3-methyl-2,4-pentadien-1-bromide (3.2 g). This bromide in benzene (15 ml) was exposed to triphenylphosphine (3.5 g) in more benzene (10 ml) and then heated to reflux, cooled and treated with ether (50 ml). The supernatant liquid was decanted off and the residue was dried to yield the 5-(2,6,6-trimethyl-3-oxocyclohexen-1-yl)-3-methyl-2,4-pentadien-1-triphenylphosphonium bromide (5.3g) as a glass.

EXAMPLE 15

Canthaxanthin

The crude salt 5-(2,6,6-trimethyl-3-oxocyclohexen-1-yl)-3-methyl,2,4-pentadien-triphenylphosphonium bromide (5.3 g) dissolved in dichloromethane (40 ml) containing 2,7-dimethyl-2,4,6-octatriene-1,8-dial. (650 mg) prepared from sodium (285 mg) and methanol (3 ml.) and stirred for 1 hr at −10° C (reaction conditions based on the work of Dr. Marbet, Basle).

Dilution with more dichloromethane and extraction with brine yield the crude product (5.0 g.) on removal of the solvent "in vacuo". This residue was chromatographed on silica gel (200 g), made up in benzene, yielding the carotenoid fraction (2.1 g) on elution with ethyl acetate-benzene mixtures (10% and 20%). Crystallization from methanol yielded canthaxanthin (1.35 g) mp 205°–207° C. The mother liquor material (∼700 mg) was heated at reflux in water (25 ml) for 16 hr, extracted with dichloromethane and then crystallized from methanol to give more canthaxanthin (400 mg) mp 205°–208° C; a second cycle of these mother liquors gave a further amount (50 mg) mp 109°–202°.

EXAMPLE 16

2,5,5-trimethyl-3-isobutyoxycyclopent-2-en-1-one 390 mls. of tetrahydrofuran was placed in a liter flask, cooled to −70° C. and placed under an Argon atmosphere. Add to this 326 mls. of 2.3 M n BuLi and then 84 gms. diisopropyl amine. Stir the solution for 20 minutes at −70° C. and then warm to 0° C. with an ice bath. In a separate 2 liter flask dissolve 55 grams of 2-methyl-3-isobutoxycyclopent-2-en-1-one to which the above lithium diisopropylamide and methyl iodide are added consecutely in the following manner:

| Amt. of Base Solution | Amt. of methyl iodide | Mole equivalent |
|---|---|---|
| 365 ml. | 46.2 gm. | 1.0 |
| 255 ml. | 32.4 gm. | 0.7 |
| 109 ml. | 13.8 gm. | 0.3 |
| 73 ml. | 9.2 gm. | 0.2 |
| 36.4 ml. | 4.62 gm. | 0.1 |

The base is added at −70° C. and then the methyl iodide at −70° C. The reaction mixture is warmed to room temperature and stirred for 15 minutes before the next addition of base and methyl iodide.

The mixture is worked up after the five additions by dilution with ether and washing with brine. The ether is dried and removal under vacuum to yield approximately 60 grams of crude product. The product is flask distilled (86° C. at 5 mm) and then fractionally distilled with a Goodloe column to remove the traces of mono and trialkylated material (b.p. approximately 212° C. at 320 mm). Final yield of 2,5,5-trimethyl-3-isobutoxycyclopent-2-en-1-one is 47.2 grams (79%).

EXAMPLE 17

5-(2,5,5-trimethyl-3-oxocyclopenten-1-yl)-3-methyl-2-trans-penten-4-yn-1-ol 36.8 grams of 2,5,5-trimethyl-3-isobutoxycyclopent-2-en-1-one is dissolved in approximately 200 mls. of anhydrous ether. The mixture is degassed at −70° C. and placed under an inert atmosphere. To this 137 mls. of 1.6 M n-butyl lithium in hexane is added at −70° C. and the reaction mixture is stirred for 10 minutes at −70° C. and then warmed to room temperature. The 29 gms. dialkylated enol ether 5-(2,5,5-trimethyl-3-oxocyclopenten-1-yl)-3-methyl-2-trans-penten-4-yn-1-ol is dissolved in approximately 50 mls. of anhydrous ether and added slowly at room temperature. The reaction is stirred for one hour and then diluted with ether. The ether is washed with brine, dried over MgSO$_4$ and removed under vacuum to yield 59.4 grams of crude product.

The product is then dissolved in 200 mls. of acetone and 100 mls. of 2 N H$_2$SO$_4$ (aqueous). The mixture is stirred under argon for 90 minutes. The acetone was removed under vacuum and the residue was dissolved in ether, washed with brine, dried over MgSO$_4$ and filtered through celite. The ether was removed to yield the crude alcohol (33.2 grams, approximately 103% contains some 1" Pentol). Recrystallization from isopropyl ether yielded 25.8 grams of 5-(2,5,5-trimethyl-3-oxocyclopenten-1-yl)-3-methyl-2-trans-penten-4-yn-1-ol (79.5%) of alcohol (mp 66°–68° C.).

EXAMPLE 18

5-(2,5,5-trimethyl-3-oxycyclopenten-1-yl)-3-methyl-2-trans-4-cis-pentadien-1-ol

To 50 mls. of ethyl acetate was added 3.0 grams of Lindlar catalyst, 5.0 grams of $KCO_3$ and 0.009 mls. of quinoline. The mixture was stirred under $H_2$ gas until no more hydrogen was absorbed. Then 4.4 grams of the 5-(2,5,5-trimethyl-3-oxocyclopenten-1-yl)-3-methyl-2-trans-penten-4-yn-1-ol were added and hydrogenated (1 atmosphere, 21° C., 484 mls. of $H_2$ abs. 1.01 m. equiv.). The reaction mixture obtained approximately 10% overreduced material and 5% starting material. The mixture was a yellow oil which contained 5-(2,5,5-trimethyl-3-oxocyclopenten-1-yl)-3-methyl-2-trans-4-cis-pentadien-1-ol as a crude product.

EXAMPLE 19

5-(2,5,5-trimethyl-3-oxocyclopenten-1-yl)-3-methyl-2,4-pentadien-1-triphenylphosphonium bromide The 1.64 grams of 5-(2,5,5-trimethyl-3-oxocyclopenten-1-yl)-3-methyl-2-trans-4-cis-pentadien-1-ol were dissolved in approximately 15 mls. of anhydrous ether and placed in an argon atmosphere. Then 3.6 mls. of $PBr_3$ in ether (2 ml.s of $PBr_3$/20 ml. of ether) were added slowly at −60° C. The reaction was stirred at −60° C. for approximately 45 minutes and then washed to room temperature. The reaction mixture was diluted with more ether and carefully quenched with $H_2O$. The ether layer was washed with brine and dried with $MgSO_4$. Benzene was added and the ether was removed leaving the bromide, i.e., 5-(2,5,5-trimethyl-3-oxocyclopenten-1-yl)-3-methyl-2,4-pentadiene-1-bromide in benzene (230 mls.).

To this bromide solution was added 1.95 grams of triphenyl phosphine dissolved in approximately 20 mls. of benzene. The solution was refluxed with 1½ hours. The solution was cooled and anhydrous ether was added precipitating out 5-(2,5,5-trimethyl-3-oxocyclopenten-1-yl)-3-methyl-2,4-pentadien-1-triphenylphosphonium bromide.

EXAMPLE 20

2,2'-Dinor-Canthaxanthin 1.3 grams of phosphonium salt 5-(2,3,5-trimethyl-3-oxocyclopenten-1-yl)-3-methyl-2,4-pentadien-1-triphenylphosphonium bromide was dissolved in 20 mls. of methylene chloride. 0.126 grams of 2,7-dimethyl-octa-2,4,6-triene-1,8-dial was added and the solution was brought to −10° C. under an inert atmosphere. The solution was treated with 2.38 mmoles of sodium methoxide (1.1 molar in methanol) and stirred for 40 minutes at −10° C. The methylene chloride mixture was washed with brine, dried and the solvent removed under vacuum. The crude product was refluxed in water for 16 hours and chromotographed on 140 grams of silica gel (ether/hexane was used as the eluding solvents). The desired fraction was recrystallized from MeOH at −70° C. Final yield of 2,2'-dinor-canthaxanthin was 0.140 grams (33.3%) mp 226°–299° C.

I claim:

1. A compound of the formula:

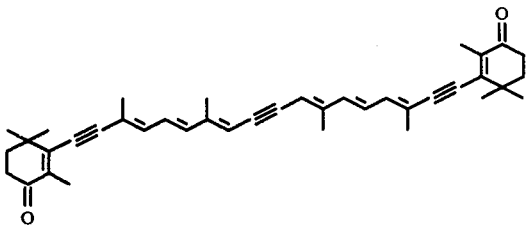

* * * * *